United States Patent [19]
Chenchik et al.

[11] Patent Number: 5,962,271
[45] Date of Patent: Oct. 5, 1999

[54] METHODS AND COMPOSITIONS FOR GENERATING FULL-LENGTH CDNA HAVING ARBITRARY NUCLEOTIDE SEQUENCE AT THE 3'-END

[75] Inventors: Alex Chenchik, Palo Alto; York Zhu, Sunnyvale; Luda Diatchenko, Palo Alto; Paul Siebert, Sunnyvale, all of Calif.

[73] Assignee: Cloutech Laboratories, Inc., Palo Alto, Calif.

[21] Appl. No.: 08/582,562

[22] Filed: Jan. 3, 1996

[51] Int. Cl.[6] ........................... C12P 19/34; C07H 21/02; C07H 21/04

[52] U.S. Cl. .................. 435/91.1; 536/23.1; 536/24.2; 536/25.3

[58] Field of Search .................. 435/91.1; 536/23.1, 536/24.2, 25.3

[56] References Cited

U.S. PATENT DOCUMENTS

| | | | |
|---|---|---|---|
| 5,219,989 | 6/1993 | Sonenberg et al. | 530/350 |
| 5,436,149 | 7/1995 | Barnes | 435/194 |
| 5,597,713 | 1/1997 | Kato et al. | 435/91.41 |
| 5,659,025 | 8/1997 | Engels et al. | 536/23.1 |
| 5,668,269 | 9/1997 | Engels et al. | 536/25.32 |

FOREIGN PATENT DOCUMENTS

| | | |
|---|---|---|
| 0346877 | 12/1989 | European Pat. Off. . |
| 0490281 | 12/1991 | European Pat. Off. . |
| 0625572 | 11/1994 | European Pat. Off. . |
| 9011369 | 10/1990 | WIPO . |
| 9117755 | 11/1991 | WIPO . |

OTHER PUBLICATIONS

Carninci et al., Genomics 37, 327–336 (1996).
Zhu et al., FASEB J. 10(6), A1126 (Abstract; Apr. 1996).
CLONTECH 1996/1997 Catalog, pp. 54–55.
CLONTECHniques, vol. XI, No. 1, Jan. 1996.
Sigma catalog, pp. 496 and 1005, 1993.
Bertling, W.M., F. Beier, and E. Reichenberger (1993) "Determination of 5' Ends of Specific mRNAs by DNA Ligase–dependent Amplification," *PCR Methods and Applications*, Oct., No. 2, New York, NY, pp. 95–99.
Chenchik, A., F. Mogadam, and P. Siebert (1995) "Full–length cDNA amplification using marathon RACE technique," *Faseb J.*, vol. 9, No. 6.
Jean Baptiste Dumas Milne Edwards et al. (1991) "Oligodeoxyribonucleotide ligation to single–stranded cDNAs: a new tool for cloning 5' ends of mRNAs and for constructing cDNA libraries by in vitro amplification," *Nucleic Acids Research*, Oct., vol. 19, No. 19, pp. 5227–5232.

(List continued on next page.)

*Primary Examiner*—Kenneth R. Horlick
*Attorney, Agent, or Firm*—Benjamin Aaron Adler

[57] ABSTRACT

Described are compositions and methods which allow for the efficient addition of a defined sequence at the 3'-end of a full-length cDNA in the course of first-strand cDNA synthesis from an mRNA template. A cDNA synthesis primer that is capable of annealing to mRNA is used to prime the first strand synthesis reaction. An oligonucleotide that is linked to the 5'-end of the mRNA serves as a short, extended template such that when the reverse transcriptase enzyme reaches the 5'-end of the mRNA, the enzyme switches templates and proceeds to transcribe through the end of the linked oligonucleotide. As a result, the single-stranded cDNA product which corresponds to the full-length mRNA, will have at the 3'-end a defined sequence which is complementary to the linked oligonucleotide. A conservative element in the oligonucleotide sequence responsible for this reaction can include 3 to 5 guanylic acid residues at the 3'-end of the oligonucleotide. The subject invention provides for the increased synthesis of full-length cDNA from mRNA templates. The full-length cDNA prepared according to the present invention can then be amplified using PCR or cloned using standard procedures.

15 Claims, 6 Drawing Sheets

OTHER PUBLICATIONS

A. B. Troutt et al. (1992) "Ligation–anchored PCR: A simple amplification technique with single–sided specificity," *Proc. Natl. Acad. Sci. USA,* vol. 89, pp. 9823–9825.

Y. Zhu et al. (1996) "CAPswitch based PCR technology for full–length cDNA library construction from small amount of RNA," *Faseb J.,* vol. 10, No. 6.

Kimmel, A.R. et al. (1987) "Preparation of cDNA and the Generation of cDNA Libraries: Overview" Methods in Enzymology: Guide to Molecular Cloning Techniques 152:307–316.

Wu, R. et al. (1987) "Adaptors, Linkers, and Methylation" Methods in Enzymology: Guide to Molecular Cloning Techniques 152:343–349.

Gubler, U., B.J. Hoffman (1983) "A simple and very efficient method for generating cDNA libraries" Gene 25:263–269.

Okayama, H. P. Berg (1982) "High–Efficiency Cloning of Full–Length cDNA" Molecular and Cellular Biology 2(2):161–170.

Edery, I. et al. (1995) "An Efficient Strategy to Isolate Full–Length cDNAs Based on an mRNA Cap Retention Procedure (CAPture)" Molecular and Cellular Biology 15(6):3363–3371.

Maruyama, K., S. Sugano (1994) "Oligo–capping: a simple method to replace the cap structure of eukaryotic mRNAs with oligoribonucleotides" Gene 138:171–174.

Fromont–Racine, M. et al. (1993) "A highly sensitive method for mapping the 5' termini of mRNAs" Nucleic Acids Research 21(7):1683–1684.

Kato, S. et al. (1994) "Construction of a human full–length cDNA bank" Gene 150:243–250.

METHODS AND COMPOSITIONS FOR GENERATING FULL-LENGTH CDNA HAVING ARBITRARY NUCLEOTIDE SEQUENCE AT THE 3'-END

FIELD OF THE INVENTION

The present invention relates to improved technology for selectively synthesizing full-length cDNA having complete sequence information of full-length mRNA.

BACKGROUND OF THE INVENTION

A basic technology in the field of molecular biology is the conversion of poly(A)+RNA (mRNA) to double-stranded (ds) complementary DNA (cDNA), which then can be inserted into a cloning vector for generating a cDNA library or expressing in an appropriate host cell. Advances in cDNA library construction technology have made possible the discovery and production of a wide range of biologically important proteins.

Main procedures for generating cDNA libraries which have been used during the last 15 years are comprehensively reviewed for example in Wu, ed. *Methods in Enzymology* (1987), vol. 152. For the most part, cDNA library construction technologies use poly(A)+RNA as a starting material. The intact poly(A)+RNA is characterized by a polyadenylated "tail" at its 3' end and a characteristic "CAP structure" at the 5' end. A critical requirement for cDNA library construction is to completely copy poly(A)+RNA to full-length cDNA and retain the complete sequence information on the structure of the protein encoded by mRNA. The "full-length" cDNA is therefore defined as a cDNA containing an entire sequence starting from a CAP site to the poly(A) tail.

One generalized and commonly used method (Gubler et al., 1983) by which the poly(A)+RNA is copied into cDNA employs reverse transcriptase, which starts at the 3' end of the mRNA from an oligo d(T) primer and proceeds towards the 5' end to generate a cDNA:mRNA hybrid. The RNA strand is then removed from the hybrid by action of RNase H and a second DNA strand is then synthesized using DNA polymerase I. The resulting heterogeneous mixture of double stranded cDNA (ds cDNA) molecules can then be cloned into recombinant DNA vector molecules using a variety of techniques. Unfortunately, this method does not allow synthesis of "full-length" cDNA because, for the majority of mRNAs, reverse transcriptase can not efficiently copy them into full-length cDNAs. The problem of "full-length" cDNA synthesis is more acute for long mRNAs as efficiency of copying is inversely proportional to the length of mRNA. Also, the current technology can generate deletions at the 5' and 3' ends of cDNA.

In an alternative approach (Okayama et al., 1982; see also Pruitt, International Patent, Appl. No. 89110816.9 of 14.06.89), poly(A) tails of mRNA molecules are first annealed to oligo (dT) linking with linearized vector DNA (vector primer). Then, the first strand of cDNA synthesized by reverse transcriptase is tailed at the 3' end by oligo dt which facilitates subsequent cloning by circularization into vector primer. This method also generate high level of cDNA clones containing truncated cDNAs due to non-full-length cDNA synthesis.

As a result, in conventional cDNA libraries, the majority of the cDNA clones do not have sequences close to the 5' end of the mRNAs. This results in a loss of important information required to make functional proteins. Two selection procedures have been developed in efforts to enrich cDNA libraries for "full-length" cDNA clones. In CAP retention procedure (CAPture) (Edery et al., 1995; Sonenberg et al., U.S. Pat. No. 5,219,989) cap-binding protein (eukaryotic initiation factor 4E) in combination with RNase A was used to purify the full-length cDNA:mRNA hybrid. Shorter duplexes corresponding to non-full-length cDNA fragments are not selected, since the cap is removed from the RNA moiety by nuclease treatment. Although the CAPture method could potentially enrich cDNA libraries for clones containing the authentic 5' ends, the yield of enriched full-length cDNA is very low, especially for long cDNAs (1–5%). The low yield can be a significant disadvantage for this technology.

In the "oligo-capping" method (Maruyama et a., 1994; Fromomt-Racine et al., 1993; Kato et al., International Patent, Publ. No. 0 625 572 A1, Appl. No. 93921061.3 of 22.09.93) the cap structure of mRNA is selectively replaced with an oligoribonucleotide, thus generating a chimeric oligonucleotide—full-length mRNA intermediates which are subsequently used for synthesis and cloning, preferably full-length cDNAs. However, this method is complicated, involving treatment of mRNA with an alkaline phosphatase, decapping mRNA with tobacco acid pyrophosphatase, and ligation of the oligonucleotide to the 5' end of mRNA by T4 RNA ligase. These multiple enzymatic steps degrade mRNA, thus generating incomplete cDNA fragments for subsequent cloning procedures. Size distribution of cDNA inserts in cDNA libraries generated by the "oligo-capping" method is less than 3 kb, which is much less than full-length mRNA size distribution (Kato et al., 1994) and indicates the low efficiency of "full-length" cDNA cloning by "oligo-capping" technology.

In summary, conventional methods for constructing of cDNA libraries containing the preferred full-length cDNA clones are restricted by low efficiency and the use of multiple, time-consuming steps. Accordingly, a simple method that would generate high quality full-length cDNA library is highly desirable.

BRIEF SUMMARY OF THE INVENTION

The present invention provides an advantageous method for synthesis and cloning of full-length cDNA, or cDNA fragments, corresponding to the complete sequence of 5'-ends of mRNAs and mapping transcriptional start sites. Specifically, the subject method provides a process for synthesis of full-length cDNA, or cDNA fragments, containing defined sequence at the 3' end (anchor), followed by a nucleotide sequence starting from a cap site of mRNA. In a preferred embodiment, the process of the subject invention comprises the following steps (see also FIG. 1):

1. Incubating a sample of poly(A)+RNA or total RNA in the presence of a cDNA synthesis primer (CDS primer) which can anneal to mRNA, an enzyme possessing reverse transcriptase activity under conditions sufficient to permit the template-dependent extension of the primer to generate a mRNA-cDNA hybrid; and
2. incubating first-strand cDNA synthesis mixture from step 1 with oligonucleotide (CAPswitch oligonucleotide), which can provide CAP-depended extension of full-length cDNA by reverse transcriptase using CAPswitch oligonucleotide as a template, and thereby adding sequence complementary to CAPswitch oligonucleotide to the 3'-end of full-length cDNA (anchored cDNA:mRNA hybrid).

Steps 1 and 2 are separated only in time, i.e., in a preferred embodiment, step 1 is followed by step 2. However, it would be understood that the first-strand cDNA synthesis mixture from step 1 can include CAPswitch oligonucleotide which will be used at step 2. Alternatively, CAPswitch oligonucleotide can be added to the reaction mixture at the time of or after first-strand cDNA synthesis.

Also within the scope of the present invention is a method for isolating a full-length cDNA fragment corresponding to a 5'-end of target mRNA using anchored cDNA:mRNA hybrid generated at step 2 as a template. This method comprises the embodiment of steps 1 and 2 with alternative step 3A or step 3B, described below:

Step 3A is: Incubating anchored cDNA:mRNA hybrid generated at step 2 with a combination of (a) primer corresponding partially or completely to sequence of CAPswitch oligonucleotide, (b) primer which is complementary to a sequence of target mRNA, and (c) an effective amount of other reagents necessary to perform PCR. The incubation is conducted under conditions sufficient to perform PCR to generate amplification product corresponding to 5'-end of a full-length fragment of target cDNA.

Step 3B is: Treating anchored cDNA:mRNA hybrid of step 2 under conditions in which a second cDNA strand is synthesized, using the first anchored cDNA strand as a template.

Also within the scope of the present invention is a method for generating cDNA libraries containing full-length cDNAs. This method uses as a template anchored cDNA:mRNA hybrid generated at step 2. This method comprises the embodiment of steps 1 and 2 with alternative step 3C or step 3D:

Step 3C is: Incubating anchored cDNA:mRNA hybrid generated at step 2 with a combination of primers corresponding partially or completely to the sequence of CAPswitch oligonucleotide and CDS primer, respectively, and an effective amount of other reagents necessary to perform PCR. The incubation is conducted under conditions sufficient to perform PCR to generate amplification product corresponding to 5'-end full-length fragment of target cDNA.

Step 3D is: Treating anchored cDNA:mRNA hybrid of step 2 under conditions in which a second cDNA strand is synthesized, using the first anchored cDNA strand as a template.

The resulting cDNA product generated at step 2 or 3 can be inserted into recombinant cloning vehicles, and hosts can be transformed with said vehicles according to the conventional methods which are well known in art (see, e.g., Kimmel et al., 1987).

The subject invention enables synthesis of full-length cDNA, which has been difficult to synthesize by conventional methods. The present invention includes the novel step 2 (see above), which can be added to standard cDNA preparation/cloning procedures which are well known in the art. Step 2 of the subject methods can provide such advantages as: it can permit discarding of incomplete cDNAs; full-length cDNAs can be readily selected for the cDNA library; and the subject methods can significantly simplify cDNA synthesis and cloning. Since the cDNA clones obtained from the full-length cDNA library prepared according to the present method contain the complete information for the primary structure of the protein, the invention also relates to a process for using the clones, obtained from said full-length cDNA library to produce the encoded proteins.

Also within the scope of the present invention are "CAPswitch" oligonucleotides useful for the preparation of cDNA libraries containing full-length cDNA clones. The CAPswitch oligonucleotides have at least two functions. One function is the ability to selectively interact with full-length intermediates of reverse transcriptase-mRNA-cDNA which are generated at the 5' end of full-length mRNA after first-strand cDNA synthesis. A second function of the CAPswitch oligonucleotides of the subject invention is as an efficient template for reverse transcriptase from the above-mentioned full-length intermediates which can allow CAP-depended extension of full-length cDNA by reverse transcriptase using CAPswitch oligonucleotide as a template. A sequence complementary to CAPswitch oligonucleotide can thereby be added to the 3'-end of full-length cDNA.

Also within the scope of the present invention are modifications in the structure or sequence of CAPswitch oligonucleotide which can provide an advantage of selective binding to CAP structure of mRNA. Another modification can include covalently binding CAPswitch oligonucleotides with a protein capable of binding the CAP structure of mRNA (see U.S. Pat. No. 5,219,984).

The invention particularly concerns the embodiments of the above methods wherein the CAPswitch oligonucleotide is represented by the following formula:

wherein dN represents a deoxyribonucleotide selected from among dAMP, dCMP, dGMP and dTMP; m represents an integer 0 and above, preferably from 10 to 50; rN represents a ribonucleotide selected from among AMP, CMP, GMP and UMP, preferably GMP; and n represents an integer 0 and above, preferably from 3 to 7. Some modifications in the structure of the primer such as replacement of 1–10 nucleotides for modified nucleotides, incorporation of terminator nucleotide (like 3'-amino NMP, 3'-phosphate NMP and so on), non-natural nucleotides, using partially double-stranded DNA containing extension of a single-stranded CAPswitch oligonucleotide sequence 5'-dN$_1$-dN$_2$- . . . dNm-rN$_1$-rN$_2$ . . . rNn-3', incorporation of restriction sites which simplify subsequent purification and cloning cDNA but still retain the main function of the CAPswitch oligonucleotide, i.e., CAP-depended extension of full-length cDNA by reverse transcriptase using CAPswitch oligonucleotide as a template are within the scope of present invention.

The subject invention includes compositions and methods for constructing cDNA libraries from nanogram quantities of total or poly A+RNA. The compositions and methods employ the CAPswitch oligonucleotides as described herein. Also included as part of the subject invention are cDNA library construction kits, for example, library construction kits which include the novel oligonucleotides according to the subject invention for use with PCR procedures.

DETAILED DISCLOSURE OF THE INVENTION

Figure 1:
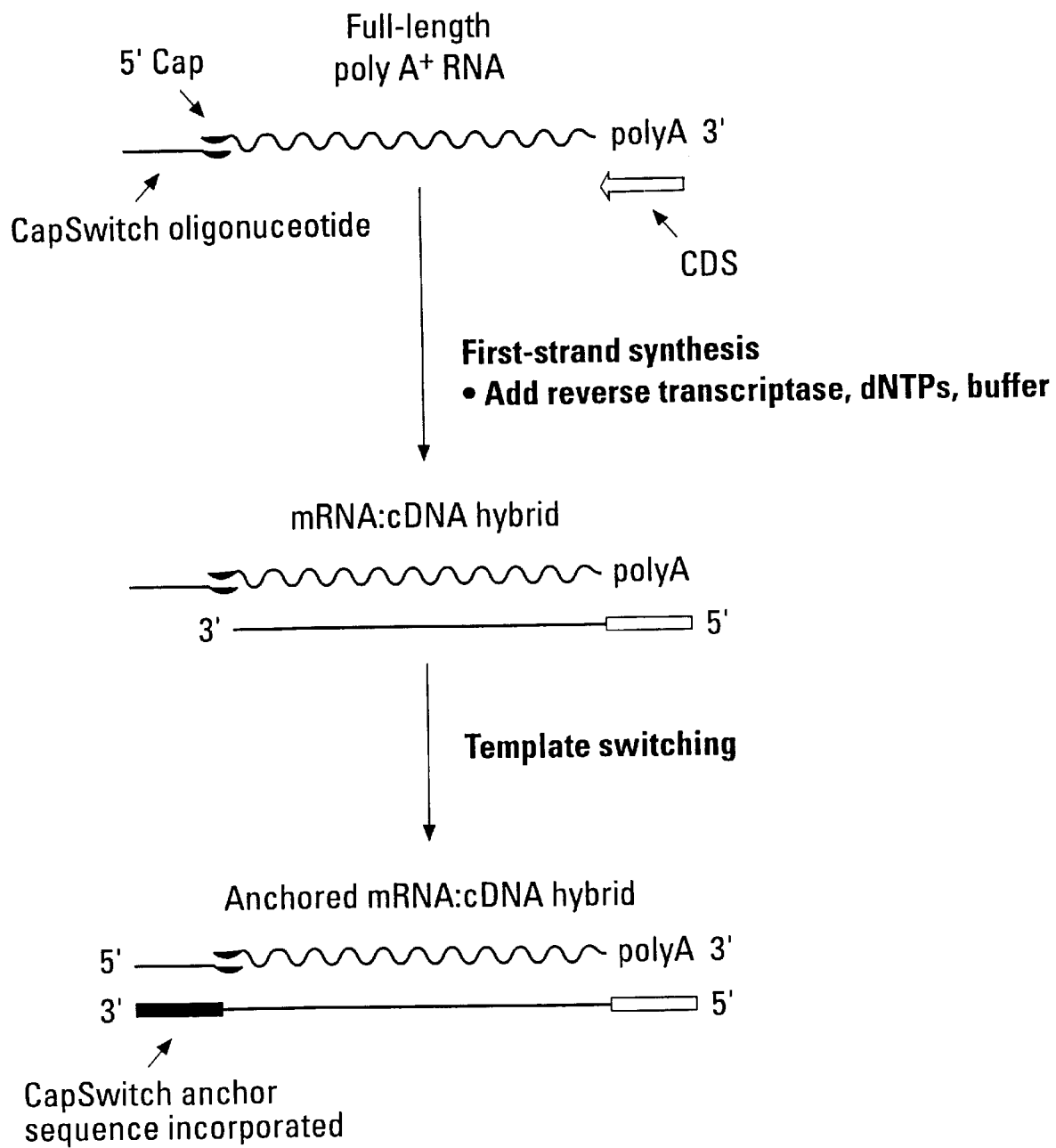
FIG. 1 shows a representation of a mechanism of template switching technology according to the subject invention.

CAPswitch technology. The CAPswitch technology of the subject invention is primarily based on the use of unique CAPswitch oligonucleotides in cDNA synthesis. The subject cDNA synthesis can include a step of first-strand cDNA from polyA+RNA using reverse transcriptase coupled with either second-strand cDNA synthesis or PCR amplification in a second step to generate a high yield of full-length ds cDNA. When included in the first-strand cDNA synthesis reaction mixture, the CAPswitch oligonucleotides create a short extended template. When reverse transcriptase stops at the 5' end of the mRNA template in the course of first-strand cDNA synthesis, it switches templates and continues DNA synthesis to the end of the CAPswitch oligonucleotide. This template switching mechanism utilizes a 7-methylguanosine CAP structure present on the 5' ends of all eukaryotic mRNAs. The resulting full-length ss cDNA incorporates at the 3' end sequence which is complementary to the complete 5' end of the mRNA, as well as the CAPswitch oligonucleotide sequence.

The template switching is one of the most frequent genomic alterations during reverse transcription of retroviral genomes. In our development of novel technology for full-length cDNA library construction we identified a structure of oligonucleotide (CAPswitch oligonucleotide) which can provide efficient template switching reaction in the course of first-strand cDNA synthesis from poly(A)+RNA using, as a donor, 5'-capped full-length mRNA and, as the acceptor, a chemically synthesized oligonucleotide. Chimeric cDNA products having an oligonucleotide sequence at the 3' end of full-length cDNA were revealed by subsequent amplification (5'-RACE) using a combination of a gene-specific primer and a primer corresponding to the oligonucleotide. One set of oligonucleotides according to our discovery, having an arbitrary sequence at the 5' end and random sequence at the 3' end, are represented by the following formulae:

CzR1 5'-d(TGTAGCGTGAAGACGACAGAA)r$(N)_{12}$-3' (SEQ ID NO. 1)
CzR2 5'-d(TGTAGCGTGAAGACGACAGAA$(N)_{11}$)r$(N)_1$-3' (SEQ ID NO. 2)
CzR3 5'-d(TGTAGCGTGAAGACGACAGAA$(N)_{11}$)-3' (SEQ ID NO. 3)
CzR4 5'-d(TGTAGCGTGAAGACGACAGAAGGATG$(N)_9$)r$(N)_1$-3' (SEQ ID NO. 4)
Na21-N4 5'-d(TGTAGCGTGAAGACGACAGAA)r$(N)_4$-3' (SEQ ID NO. 5)
Na21-N8 5'-d(TGTAGCGTGAAGACGACAGAA)r$(N)_8$-3' (SEQ ID NO. 6)
NA21-N12 5'-d(TGTAGCGTGAAGACGACAGAA)r$(N)_{16}$-3' (SEQ ID NO. 7)

wherein d( . . . ) represents a deoxyribonucleotide sequence; d( . . . $(N)_{11}$) represents a random deoxyribonucleotide sequence 11 bases long of dAMP, dGMP, dCMP and dTTP in each base position; r$(N)_{1-16}$ represents a random sequence of 1–16 bases long of AMP, GMP, CMP and UMP in each base position.

Based on the efficiency of amplification of 5'-ends (5'-RACE) of four human cDNAs (smooth muscle α-actin, smooth muscle γ-actin, cytoskeletal γ-actin and transferrin receptor and model RNAs with and without cap structure at the 5' end), and subsequent sequence analysis of amplified product, we found conservative structures at the 3' end of an oligonucleotide which can generate a highly efficient CAP-dependent template switching reaction. Mutation analysis in conservative and non-conservative part of oligonucleotide sequence (see the sequences of additional analyzed CAPswitch oligonucleotides, SEQ ID NOS. 19–66 Presented in Table 1) revealed that:

1. The highest efficiency of CAP-dependent template switching was shown by a basic DNA-RNA chimeric CAPswitch oligonucleotide having an arbitrary sequence at its 5' end and a conservative oligo rG sequence at the 3' end. This oligonucleotide is represented by the general formula:

5'-$dN_{18-21}$-$rG_{3-5}$-3' wherein dN represents an arbitrary deoxyribonucleotide sequence 18–21 bases long; and $rG_{3-5}$ represents an oligo rG sequence 3–5 bases long. The oligo rG sequence is responsible for the main template switching function of the CAPswitch oligonucleotide. The arbitrary deoxyoligonucleotide sequence can be useful for subsequent cDNA synthesis and cloning steps. The presence of the CAP structure at the 5' end of mRNA is a necessary requirement for template switching reaction.

2. There are a set of possible modifications in the structure of basic CAPswitch oligonucleotide which can change the template switching efficiency but still retain the main function of the CAPswitch oligonucleotide, i.e., CAP-dependent extension of full-length cDNA by reverse transcriptase using CAPswitch oligonucleotides as a template. The modified oligonucleotides can be used as alternative CAPswitch oligonucleotides. The following rules summarize these modifications according to the subject invention:

2a. Using a shorter (1–2 bases) oligo rG 3' end sequence, replacement of one or several rG residue(s) for rA, rC or rU or replacement of oligo rG for oligo dG reduces efficiency of the basic structure; the longer oligo rG sequence (7–9 bases) does not significantly influence template switching efficiency.

2b. Modification of the 3' terminal G at the 3'-OH group of ribose residue by amino, biotin, phosphate or glycerol group can significantly reduce background in subsequent PCR step (step 3A).

2c. Changes in the sequence of the arbitrary portion of the basic CAPswitch oligonucleotide, including restriction site (s), does not significantly influence template switching efficiency. Using a longer (22–40 bases) arbitrary sequence at the 3' end does reduce the efficiency of template switching; shorter (15–17 bases) sequences slightly increase the efficiency of template switching but make subsequent PCR steps (step 3A, 3C) less efficient.

2d. A person skilled in this art having the benefit of the current disclosure would recognize that other modifications in the structure of the basic CAPswitch oligonucleotide can increase the efficiency and specificity of CAP-dependent switching reaction. For example, using aptamer (random oligonucleotide) selection technology (Kenan et al., 1994) it is possible to find ribonucleotide or deoxyribonucleotide sequences of the arbitrary portion of the basic CAPswitch oligonucleotide which possess efficient binding to the CAP structure and therefore increase efficiency of the template switching reaction. The same result can be achieved by replacement of natural nucleotide(s) for modified nucleotides in order to increase affinity of CAPswitch oligonucleotides to the CAP structure.

Chimeric protein-CAPswitch oligonucleotides can also be constructed so that the protein portion recognizes and binds the CAP structure, which can increase efficiency of the template switching reaction. These cap binding proteins or protein portions are well known in the art and preferably include antibodies against the CAP structure and eukaryotic initiation factor 4E (eIF-4E).

Combination of CAPswitch technology with standard, conventional procedures for cDNA library construction. Another advantage of using the CAPswitch technology is the high flexibility of this procedure which makes it possible to use this new technology with conventional cDNA cloning procedures well known in art. Advantageously, the subject CAPswitch technology can eliminate multiple enzymatic or purification procedures used in conventional procedures. The CAPswitch protocol can provide CAP-dependent automatic and direct addition of a CAPswitch oligonucleotide sequence in the course of first-strand cDNA synthesis to the 5' end of mRNA:cDNA hybrid. As discussed in detail, below, the CAPswitch technology can be combined with well-known procedures for cDNA synthesis and cloning. It will be apparent to those skilled in the art that the order of some of the individual steps, the exact structure of CDS primers, and the vectors used for cDNA library construction protocol can be varied. Any such variations which allow to clone full-length cDNA but include CAPswitch technology as one of the step are within the scope of the invention. The description below details only preferred steps which efficiently result in generation of full-length cDNA cloning.

Step 1. First-strand cDNA synthesis. Using the subject method with conventional procedures, first-strand cDNA synthesis can be carried out using an annealed complex CDS primer:mRNA as a template catalyzed by reverse transcriptase, or DNA polymerase possessing reverse transcriptase activity, in the presence of adequate amounts of other components (four deoxyribonucleoside triphosphates, Mg2+, optimal buffer) necessary to perform the reaction. As a starting material for cDNA synthesis, poly(A)+RNA or total RNA from yeast and higher organisms such as plants or animals can be used. CAPswitch technology provides some modification in this basic protocol.

First-strand cDNA synthesis can include CAPswitch oligonucleotides, described in detail above, but are not a necessary component for first-strand synthesis. Alternatively, the CAPswitch oligonucleotides can then be used for the template switching step which follows the first-strand synthesis step. Thus, CAPswitch oligonucleotide can be included in the first-strand reaction composition (CDS primer annealing step or added together with reverse transcriptase, see Example 1) or added in the course of, or after completion of, first-strand cDNA synthesis reaction.

Depending on the strategy for cDNA cloning (see, e.g., Wu, ed. *Methods in Enzymology* (1987), vol. 152.) several CDS primer structures can be used for first-strand cDNA synthesis catalyzed by reverse transcriptase and using poly (A)+RNA as a template. The CDS primer can be selected from single-stranded oligonucleotide, double-stranded oligonucleotide with single-stranded portion (primer-restriction-end or PRE, adapter, as described by Coleclough et al., 1985), or vector primer, representing ds vector with a single-stranded portion (described by Okayama et al., 1982). In all three cases, a single-stranded portion of CDS primer is responsible for binding with poly(A)+RNA and initiating the first-strand cDNA synthesis. The CDS primer can also bind with a different portion of the poly(A)+RNA. Preferably, for full-length cDNA library construction, a CDS primer containing the oligo dT tail at the 3' end can be annealed to the poly(A) portion of mRNA. For rapid amplification or cloning of 5' cDNA ends and for selective cloning of particular genes, the CDS primer can possess a random sequence or arbitrary sequence which corresponds to a particular sequence of a target gene which is to be cloned.

The subject invention particularly concerns the embodiments of the above methods wherein the CDS primer can be annealed to:

1a. The poly(A) tail of poly(A)+RNA. The primer can be selected from an oligonucleotide, any partially double-stranded DNA fragment, or any linear vector primer. In a preferred embodiment, the oligonucleotide primer has the sequence 5'-$dN_1$-$dN_2$- . . . dNm-dTn-$dN_1$-$dN_2$- . . . dNp-3', wherein m represents an integer 0 and above, preferably from 0 to 20; n represents an integer 8 and above, preferably from 8 to 30; p is preferably from 0 to 3; dN represents a deoxyribonucleotide selected from or represent mixture of dAMP, dCMP, dGMP, and dTMP; dT represents dTMP. Some modifications in the structure of the primer such as replacement of 1–10 nucleotides for modified nucleotides, ribonucleotides, non-natural nucleotides, incorporation of restriction sites which simplify subsequent purification and cloning cDNA but still retain the main function of the primer, i.e., priming activity from poly(A) portion of poly(A)+RNA, are within the scope of present invention. Using a partially double-stranded DNA primer or linear plasmid vectors having a single-stranded tail sequence 5'-$dN_1$-$dN_2$- . . . dNm-dTn-$dN_1$-$dN_2$- . . . dNp-3', described above, and possessing priming activity for first-strand cDNA synthesis from poly(A) portion of poly(A)+RNA, are also considered as part of the subject invention. In order to simplify the cloning procedure, the CAPswitch oligonucleotide can be attached to the other end of vector primer. In this case, the vector primer will possess at one end a sequence corresponding to the CDS primer and, at the other end, the CAPswitch oligonucleotide (CAPswitch-vector primer technology). Subsequent cDNA synthesis and automatic template switching will generate cDNA:vector chimeric product, which can be easily cloned as described Okayama et al., 1982.

1b. Inner, non-poly(A) portion of the mRNA. These oligonucleotide primer(s) have the general formula $dN_1$-$dN_2$- . . . dNq, where dN represents a deoxyribonucleotide selected from among dAMP, dCMP, dGMP, and dTMP or represent a mixture of 2–4 of these bases; and q represents integer 6 and above, preferably from 6 to 50. These primers can have a random sequence, i.e., annealed to all mRNAs, an arbitrary sequence, i.e., annealed to at least one arbitrary mRNA, or a sequence complementary to at least one mRNA. Also, the sequence of these primer(s) can include a restriction site(s) or modified bases (for example, biotinylated) to facilitate subsequent purification or cloning procedure.

Step 2. Second-strand cDNA synthesis and/or PCR amplification. First-strand cDNA synthesis based on CAPswitch technology generates a full-length (or the corresponding 5' end of a full-length fragment) mRNA:cDNA hybrid molecule intermediates flanked by a CDS primer at its 3' end, and a CAPswitch oligonucleotide at its 5' end. Such intermediates can be easily converted to a ds cDNA form suitable for subsequent cloning using conventional procedures. These procedures are well known and include:

1. Direct amplification of full-length cDNA by combination of PCR primer corresponding CDS and CAPswitch flanking portions of mRNA:cDNA hybrid and effective amount of other reagents under conditions necessary to perform PCR. Preferably, the conditions are those developed for amplification of long nucleic acid sequences and described by Cheng (International Patent (1995)) and Barnes (U.S. Pat. No. 5,436,149 of Jul. 25, 1995).

2. Replacement of the mRNA portion of the mRNA:cDNA hybrid with a second-strand cDNA essentially as described by Okayama et al. (1982) and Gubler et a. (1983). This process entails digestion of the RNA with a ribonuclease such as *E. coli* RNase H, repair synthesis using a DNA polymerase having the activities of DNA polymerase I, and ligation. The procedure depends on the structure of the CDS primer used for the first-strand cDNA synthesis. Second-strand cDNA synthesis can be carried out using as a template mRNA:cDNA hybrid or mRNA:cDNA:vector chimeric product using vector primer for first-strand synthesis (CAPswitch-vector primer technology, see above). Alternatively, mRNA:cDNA hybrid generated by PRE adaptor strategy, described above, can be digested at the 5' and 3' flanking sequences, which correspond to PRE adaptor and CAPswitch oligonucleotide by at least one restriction enzyme, and then ligated into a conventional vector digested by the same restriction enzyme(s). Any restriction enzyme(s) can be used as long as it does not cut within mRNA:cDNA hybrid.

Step 3. Cloning into vector. In the case of using a vector primer (CAPswitch-vector primer) or PRE adaptor strategy, the ds cDNA generated after second-strand cDNA synthesis is already inserted into the vector and does not require this step. Preferably, when oligonucleotide CDS primer is used, the ds cDNA prepared in the second step by PCR or by mRNA replacement technology can be ligated with adaptors or digested with restriction enzyme(s) in sequences corresponding to CDS and CAPswitch oligonucleotide flanking portions, thus generating ds cDNA molecules which will be ligated to any conventional cloning vector (including plasmid, cosmid, phage and so on) after digesting it with the same restriction enzyme(s).

Then, recombinant DNA molecules comprising a full-length cDNA library can be introduced into prokaryotic hosts and, optionally, eukaryotic hosts, useful in the high frequency cloning of full-length ds cDNA and in the generation of ss cDNA therefrom.

Once cloning is completed according to the invention, the desired clone(s) can be detected by labeled probe, monoclonal or polyclonal antibodies prepared against the product in a conventional immunoassay or enriched for desired target by hybridization selection approach, described for example by Li et a. in International Patent WO 95/04745 of Aug. 9, 1994.

Summary. Use of CAPswitch oligonnucleotides in cDNA synthesis and cloning significantly simplifies and improves technology of full-length cDNA library construction. The main benefits are as follows:

1. The one-stage procedure which includes first-strand cDNA synthesis and addition of a defined sequence to the 3' end of cDNA which significantly reduces the number of steps (from 5–7 to 2–3 steps) necessary for conventional PCR-based standard cDNA library construction technology. A lower number of steps means that the novel CAPswitch-based technology is more efficient, easier, less labor-intensive, and more reproducible than conventional cDNA library construction methods.

2. In accordance with the present invention, the CAP-dependent template switching mechanism provides significantly more efficient technology for synthesizing full-length cDNA and generating cDNA libraries mostly containing full-length cDNAs. The CAPswitch technology can provide a novel method for readily selecting the full-length cDNAs to be cloned in the cDNA library.

Following are examples which illustrate procedures for practicing the invention. These examples should not be construed as limiting. All percentages are by weight and all solvent mixture proportions are by volume unless otherwise noted.

EXAMPLE 1

Figure 2:
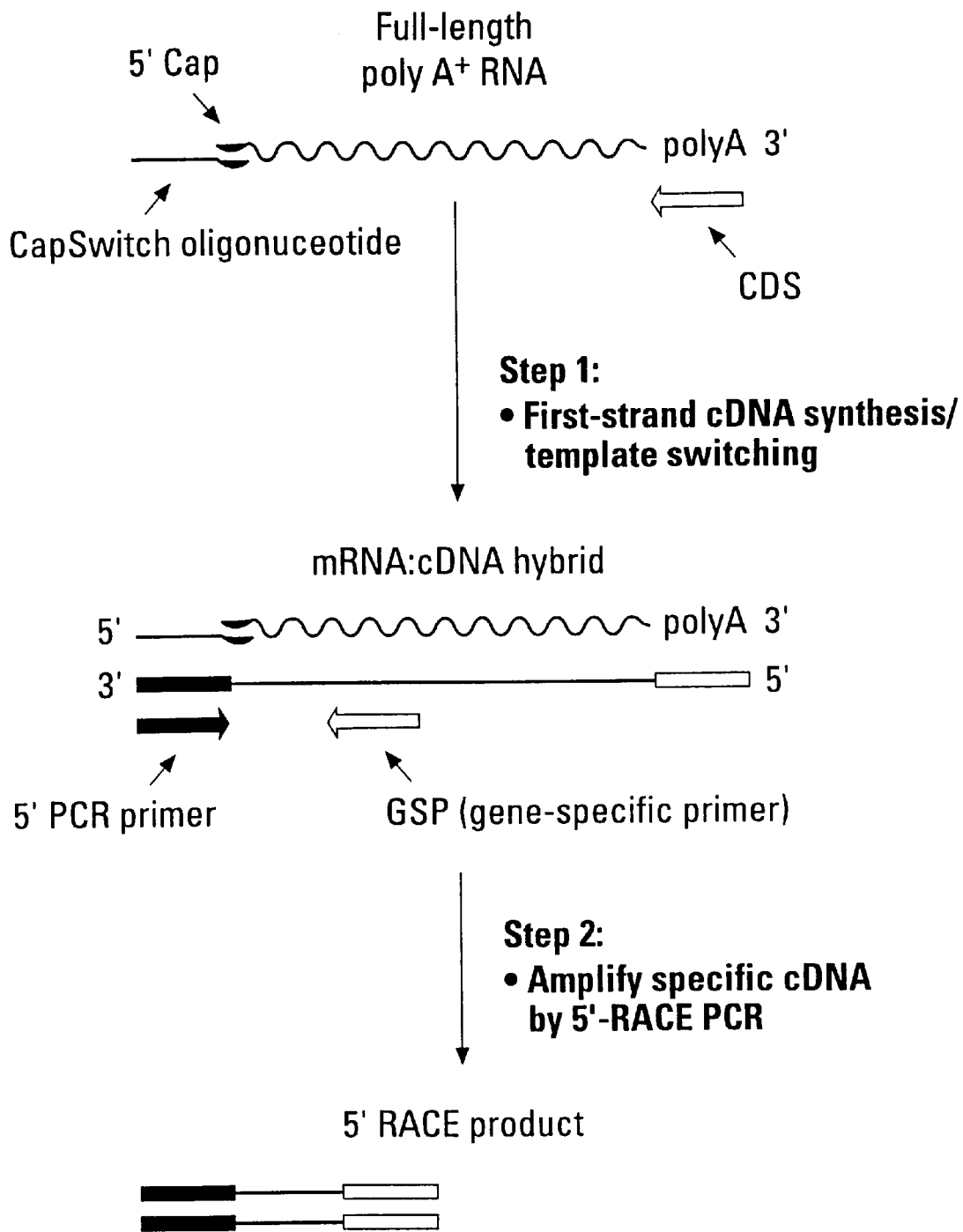
FIG. 2 shows a representation of a procedure using the CAPswitch-based technology according to the subject invention for cloning 5'-end sequence of full-length DNA.

Preferred Method for Cloning 5'-end Sequences of Full-Length cDNA Based on CAPswitch Technology Obtaining a full-length cDNA is one of the most important, and often one of the most difficult, tasks in characterizing genes. Traditional methods for cDNA library construction usually produce only partial cDNA fragments. To facilitate recovery of the rest of the coding sequence, an in vitro method for the rapid amplification of cDNA ends (RACE) was proposed in 1988 (Frohman et al., 1988). In spite of various modifications which have been developed, the current RACE technologies are complicated and inefficient. The CAPswitch technology which is an object of the present invention provides a method which significantly simplifies and makes more efficient the 5'-RACE procedure. The flow chart which describes CAPswitch-based 5'-RACE procedure is shown in FIG. 2, and the preferred protocol is described below. Some obvious modifications in protocol, e.g., using other enzymes possessing similar enzymatic activities for first-strand synthesis step and PCR, using other sequences of CDS primer and CAPswitch oligonucleotide, using for first-strand synthesis a CDS primer instead of a gene-specific primer, all fall within the scope of the present invention.

Step. 1 First-strand cDNA synthesis-template switching procedure. 10 pmol of cDNA synthesis primer (oligo d(T) primer)

CDS1: 5'-d(TCTAGAATTCAGCGGCCGC(T)$_{30}$VN)-3' (SEQ ID NO. 8)

(where V=G or A or C; N=G or A or T or C) and 50 pmol of CAPswitch oligonucleotide (CSO1):

CSO1: 5'-d(CTAATACGACTCACTATAGGGC)r(GGGp)-3' (SEQ ID NO. 9)

(where p is 3'-phosphate group) were annealed to 1 μg of human placenta poly(A)$^+$RNA (CLONTECH), in a volume of 5 μl of deionized water, by heating the mixture for 2 minutes at 70° C., followed by cooling on ice for 2 minutes. First-strand cDNA synthesis was then initiated by mixing the annealed primer-RNA with 200 units of M-MLV RNase H- reverse transcriptase (SuperScript II reverse transcriptase, Life Technologies) in a final volume of 10 μl, containing 50 mM Tris-HCl (pH 8.3 at 22° C.); 75 mM KCI; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and then cooled on ice. We also synthesized first-strand cDNA using random d(N)$_6$ primers (500 ng) or human beta-actin antisense gene-specific primer:

ACT1: 5'-d(ACTCGTCATACTCCTGCTTGCTGATCCA-CATCTGC)-3' (SEQ ID NO. 10)

or human transferrin receptor antisense gene-specific primer:

TFR1: 5'-d(GTCAATGTCCCAAACGTCACCAGAGA)-3' (SEQ ID NO. 11) instead of the oligo d(T) primer.

The reaction mixture was then diluted 500-fold by addition of 5 ml of 10 mM Tricine-KOH (pH 8.5 at 22° C.) and 0.1 mM EDTA, incubated at 94° C. for 1.5 min, cooled on ice, and stored at −20° C.

Step 2. 5'-RACE. PCR amplification was performed using the Advantage KlenTaq Polymerase Mix (CLONTECH). This kit contains a mixture of KlenTaq-1 and DeepVent DNA polymerases (New England Bio Labs) and TaqStart antibody (CLONTECH). The TaqStart antibody provides automatic hot-start PCR. Amplification was conducted in a 50-μl volume containing 5 μl of diluted first-strand cDNA; 40 mM Tricine-KOH (pH 9.2 at 22° C.); 3.5 mM Mg(OAc)$_2$; 10 mM KOAc; 75 μg/ml BSA; 200 μM each of dATP, dGTP, dCTP, and dTTP; 0.2 μM each of CAPswitch primer (CSP1): 5'-d(CTAATACGACTCACTATAGGGC)-3' (SEQ ID NO. 12) and gene-specific primer (GSP 1 for beta-actin or transferrin receptor); and 1 μl of 50× KlenTaq Polymerase Mix. Temperature parameters of the PCR reactions were as follows: 1 minute at 94° C. followed by 5 cycles of 94° C. for 30 seconds and 72° C. for 5 minutes; then 5 cycles of 94° C. for 30 seconds and 70° C. for 5 minutes; 25 cycles of 94° C. for 30 seconds and 68° C. for 5 minutes; followed by a 10-minute final extension at 68° C. PCR products were examined on 1.2% agarose/EtBr gels in 1× TBE buffer. As a DNA size marker we used a 1 kb DNA Ladder (Life Technologies).

Both human beta-actin and transferrin receptor cDNA 5'-RACE reaction generate a single band which correspond to the expected size of full-length amplified 5'-RACE product. Subsequent cloning and sequence analysis of 18 randomly picked 5'-RACE clones confirm their identity to beta-actin and transferrin receptor 5'-end fragments. Moreover, 5'-end sequences of amplified 5'-RACE product exactly correspond to sequences of full-length beta-actin and transferrin receptor mRNAs followed by sequences corresponding to CAPswitch oligonucleotide. This example illustrates that CAPswitch 5'-RACE can be efficiently used not only for amplification of full-length 5'-end sequences of cDNAs but also for exact mapping of transcriptional start sites.

EXAMPLE 2

CAPswitch PCR-Based Technology for Full-Length cDNA Library Construction

Figures 1, 3:
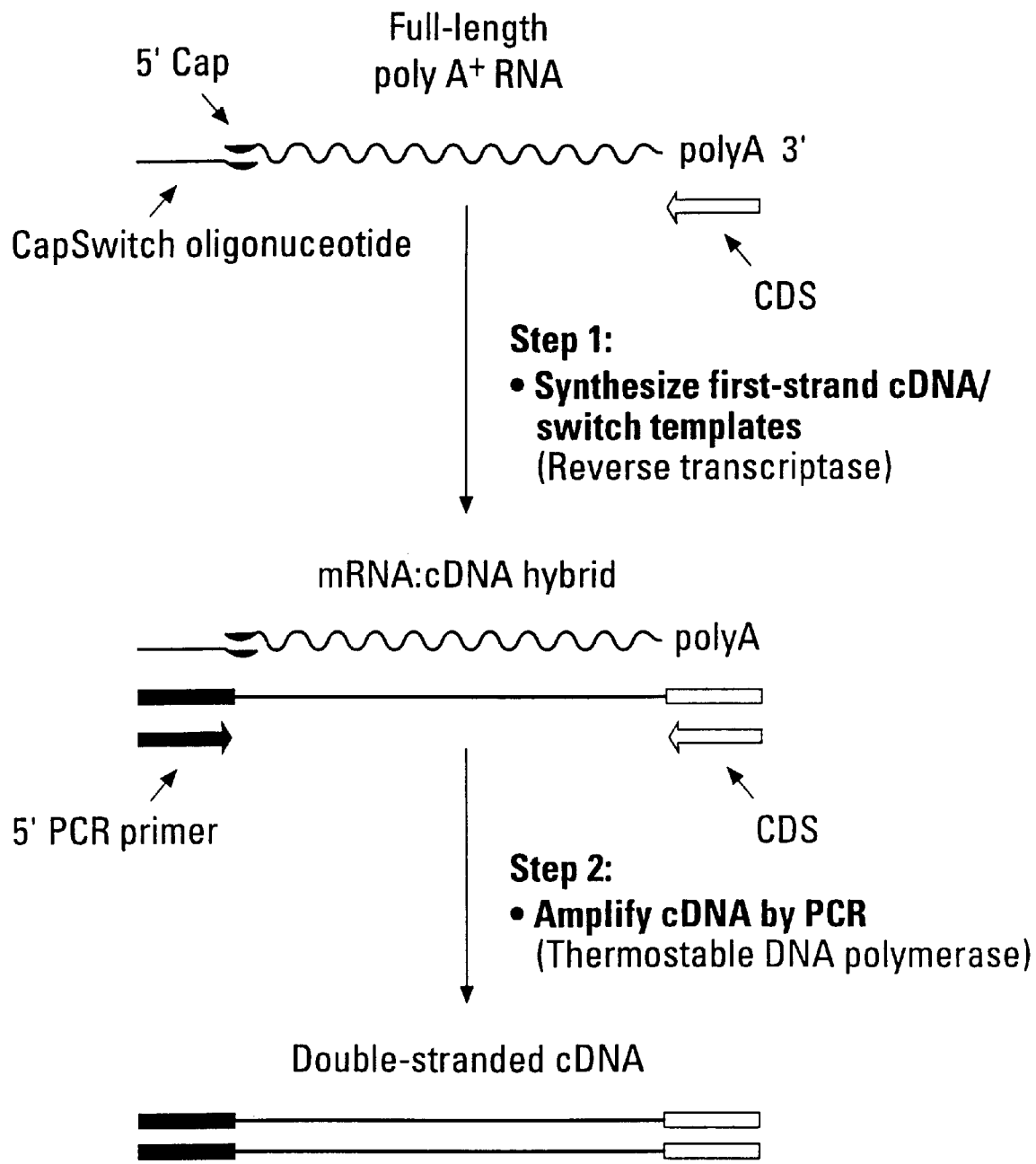
FIG. 3 shows a representation of PCR-based CAPswitch technology for full-length cDNA library construction according to the subject invention.
Figures 2, 3:
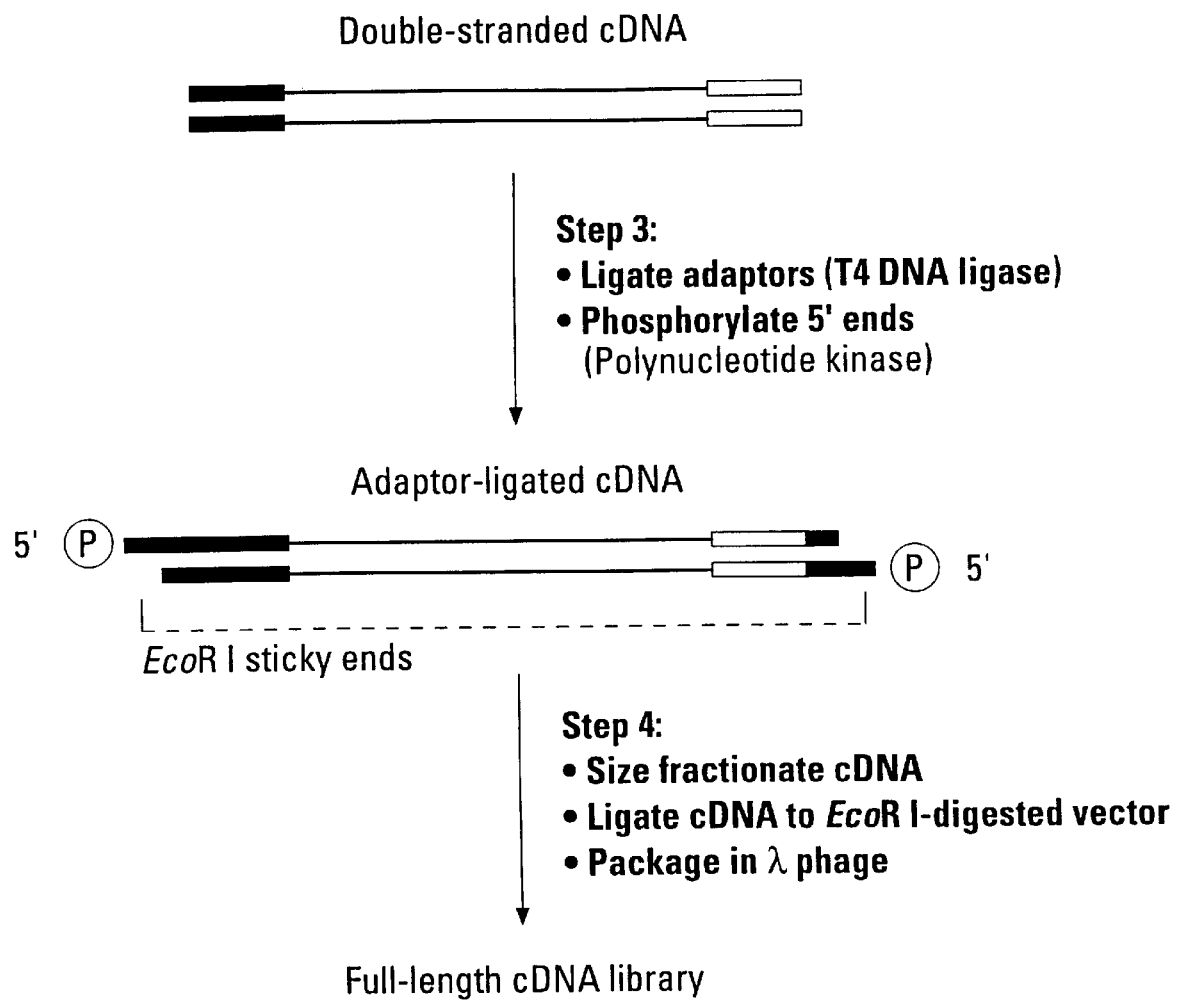

CAPswitch technology can be effectively used for construction of cDNA libraries using as a template 10–100 ng of total RNA. Any conventional procedure well known in art can be used to purify this small amount of total RNA from 10–50 mg of "difficult" cells or tissues, like human biopsy tissues, pathogenic microorganisms, tissues at different developmental stages and so on. The flow chart in FIG. 3 shows the main step of this procedure. It will be apparent to those skilled in the art that some individual non-essential steps, structure of CDS primer, CAPswitch oligonucleotide and adaptors shown in FIG. 3 can be varied without changing the efficiency of the whole procedure. For example, instead of the adaptor ligation step (step 3), ds cDNA generated by PCR can be digested by rare cutting restriction endonuclease(s) in sequences corresponding CDS and CAPswitch oligonucleotide flanking portions and cloned directly into vector. Also, other conventional procedures well known in the art for direct cloning of PCR product, such as TA-cloning vector, blunt end ligation, and the like, can be used for cloning and generation of CAPswitch full-length cDNA libraries. Any such variations in the preferred protocol which are based on using CAPswitch technology are within the scope of the invention.

Step 1. First-strand synthesis—template switching. 10 pmol of cDNA synthesis primer (oligo d(T) primer) CDS1:
5'-d(TCTAGAATTCAGCGGCCGC(T)$_{30}$VN)-3' (SEQ ID NO. 8)
(where V=G or A or C; N=G or A or T or C) and 10 pmol of CAPswitch oligonucleotide (CSO2):
CSO2: 5'-d(CTAATACGACTCACTATAGGGC)r(GGG)-3' (SEQ ID NO. 13)
were annealed to 100 ng of human skeletal muscle Total RNA (CLONTECH) in a volume of 5 μl of deionized water by heating the mixture for 2 minutes at 70° C., followed by cooling on ice for 2 minutes. First-strand cDNA synthesis was then initiated by mixing the annealed primer-RNA with 200 units of M-MLV RNase H-reverse transcriptase (SuperScript II reverse transcriptase, Life Technologies) in a final volume of 10 μl, containing 50 mM Tris-HCl (pH 8.3 at 22° C.); 75 mM KCl; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and then cooled on ice.

Step 2. Generation of full-length cDNA by PCR. PCR amplification of full-length cDNA was performed using the Advantage KlenTaq Polymerase Mix (CLONTECH). Amplification was conducted in a 100-μl volume containing 2 μl of first-strand cDNA; 40 mM Tricine-KOH (pH 9.2 at 22° C.); 3.5 mM Mg(OAc)$_2$; 10 mM KOAc; 75 μg/ml BSA; 200 μM each of dATP, dGTP, dCTP, and dTTP; 0.2 μM each of CAPswitch primer (CSP1) and CDS1 primer 1; and 1 ml of KlenTaq Polymerase mix. Temperature parameters of the PCR reactions were as follows: 1 minute at 95° C. followed by 20–22 cycles of 95° C. for 15 seconds and 68° C. for 5 minutes; followed by a 10-minute final extension at 68° C. PCR products were examined on 1.2% agarose/EtBr gels in 1× TBE buffer. As a DNA size marker we used a 1 kb DNA Ladder (Life Technologies).

Step 3. Adaptor ligation. The 50 μl of ds cDNA generated at the PCR step were combined with 2μl of Proteinase K (2 mg/ml) and incubated at 45° C. for 1 hour, followed by a denaturation step at 70° C. for 10 minutes. Then, 3 μl (15 units) of T4 DNA polymerase were added to the reaction mixture and additionally incubated at 16° C. for 30 minutes. ds cDNA was then precipitated by addition of a half volume of 4 M ammonium acetate (about 35 μl) and 3.7 volumes of 95% ethanol (about 260 μl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 16 μl of deionized water. The ds cDNA was then ligated to an adaptor overnight at 16° C. under the following conditions: 16 μl of ds cDNA solution, 50 mM Tris-HCl (pH 7.8 at 22° C.), 10 mM MgCl$_2$, 1 mM DTT, 1 mM ATP, 5% polyethylene glycol (M.W. 8,000), 2 μM of adaptor (Ad1):
Ad1: 5'-d(AATTCGCGGCCGCGTCGAC)-3' (SEQ ID NO. 14)
3'-d(GCGCCGGCGCAGCTGp)-5' (SEQ ID NO. 15)
(where p-3'-phosphate group) and 1 unit of T4 DNA ligase (Life Technologies) in a total volume of 30 μl. The ligation mixture was then stopped by addition of 70 μl of 10 mM EDTA. The ds cDNA was extracted once with phenol/chloroform/isoamyl alcohol (25:24:1, vol/vol), once with chloroform/isoamyl alcohol (24:1, vol/vol), and then precipitated by addition of 10 μl of 3 M sodium acetate and 250 μl of 95% ethanol. After vortextng, the tube was immediately centrifuged at 14,000 r.p.m. in a microcentrifuge for 20 minutes. The pellet was washed with 80% ethanol without vortexing, centrifuged as above for 10 minutes, air dried, and dissolved in 20 μl of deionized water. The adaptor ligated ds cDNA was then phosphorylated at 37° C. for 30 minutes under the following conditions: 20 μl of adaptor-ligated ds cDNA solution, 50 mM Tris-HCl (pH 7.8 at 22° C.), 10 mM MgCl$_2$, 1 mM DTT, 1 mM ATP, 30 units of T4 polynucleotide kinase (Epicenter Technology) in a final volume 30 μl. Then phosphorylation reaction was terminated by adding 2 μl of 0.2 M EDTA and heat inactivated at 70° C. for 15 minutes.

Step 4. cDNA Size fractionation and cloning. Phosphorylated adaptor-ligated ds cDNA generated at the previous step was fractionated on the 1.2 ml Sephacryl S500 0 (Phamacia) gel filtration column equilibrated by 10 mM Tris-HCl (pH 7.4), 30 mM NaCl, 0.5 mM EDTA. Size distribution of cDNA in the fractions was analyzed by 1.1% agarose/EtBr gel alongside a 1 kb DNA size marker (Life Technologies). Fractions corresponding to cDNA sizes longer than 0.5 kb were pooled together (total volume 250 µl) and precipitated by adding 1/10 volume (25 µl) of 3 M sodium acetate, 1.5 µl of 20 mg/ml glycogen and 2.5 volume (400 µl) of 95% ethanol.

After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 15 µl of deionized water. The ds cDNA was then ligated to the λgt11 EcoRI vector arm (CLONTECH) overnight at 16° C. under the following conditions: 5 µl of ds cDNA solution, 50 mM Tris-HCl (pH 7.8 at 22° C.), 10 mM MgCl$_2$, 1 mM DTT, 1 mM ATP, 5% polyethylene glycol (M.W. 8,000), 2.5 µg of λgt11 EcoRI arms, and 2.5 units of T4 DNA ligase (Life Technologies) in a total volume of 25 µl. The ligation mixture was then packaged using standard protocol described in the laboratory manual by Sambrook et al. (1989).

In order to confirm the high quality of the library generated by CAPswitch technology, 50 recombinant phage clones were selected at random for the determination of insert size. Size distribution of inserts was in the range of 0.5–4.5 kb with a maximum of 2.0–3.0 kb that correspond to size distribution of skeletal muscle poly(A)+RNA in Total RNA used for cDNA library construction. The same 50 inserts were sequenced using Delta Tth DNA polymerase Sequencing kit (CLONTECH). Ten of the sequences were identified in a search of the GenBank database. They are transferrin receptor, ribosomal protein L7, myosin light chain 2, LIM domain protein, ATPase factor 6, cytochrome C oxidase, cytoskeletal γ-actin, smooth muscle α-actin, and smooth muscle γ-actin. For three cDNAs the sequences of the clones were longer than published in GenBank. For seven cDNAs, their sequences exactly corresponded to full-length mRNA sequences starting from the cap site.

These data show that CAPswitch based technology for cDNA library construction generate a high quality cDNA library with a very high level of full-length cDNA clones.

EXAMPLE 3

Figures 1, 4:
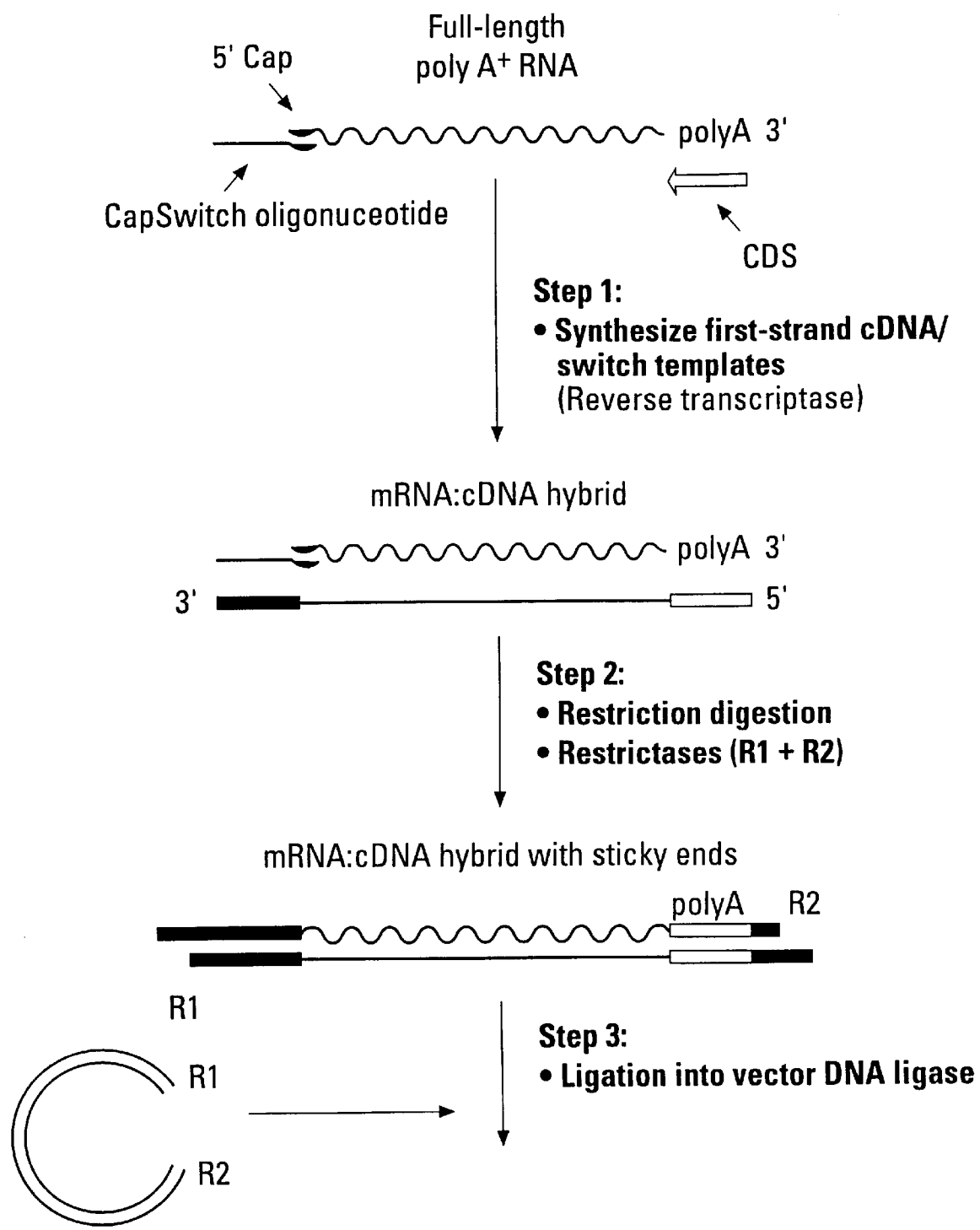
FIG. 4 shows a representation of CAPswitch full-length cDNA library construction technology based on PRE adaptor-primer strategy.
Figures 2, 4:
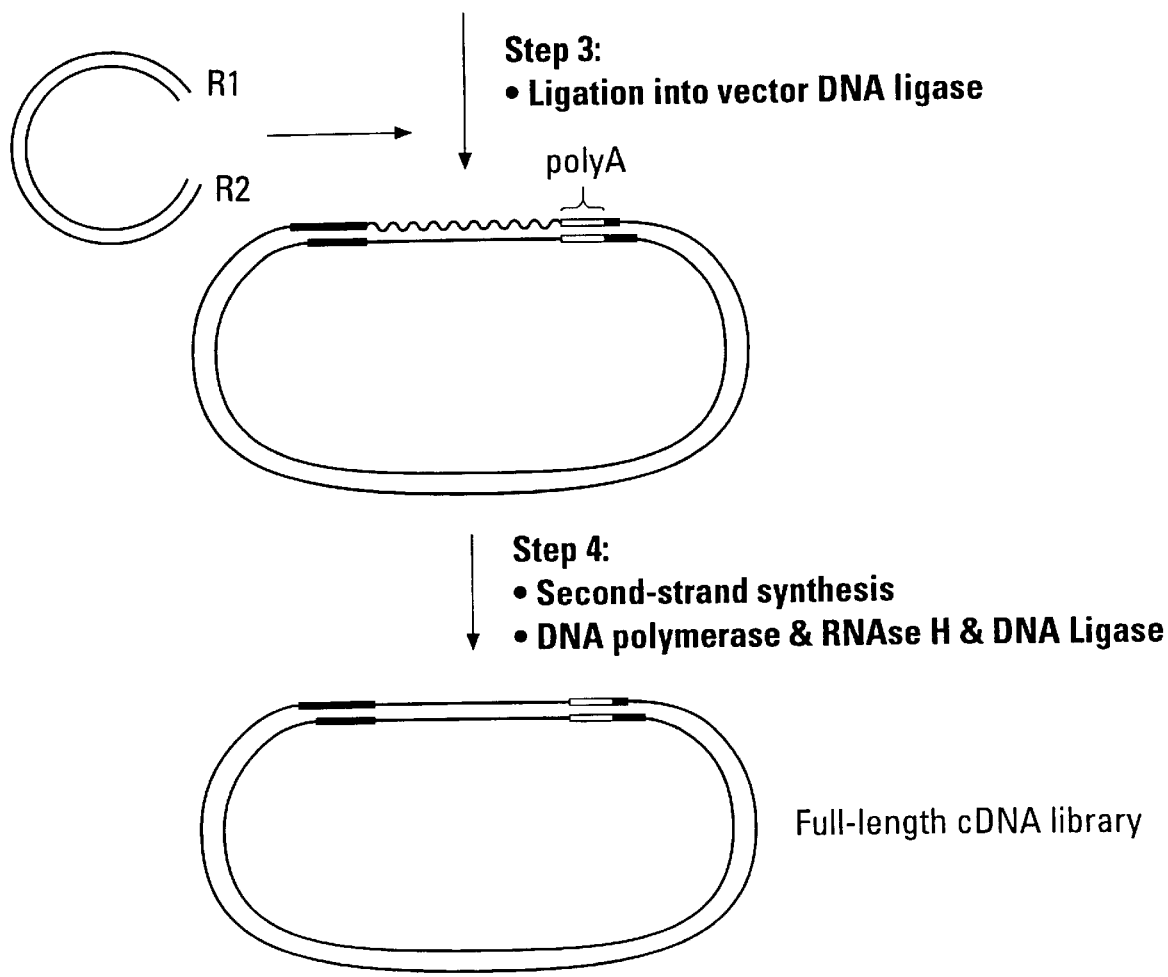

CAPswitch Full-Length cDNA Library Construction Using PRE Adaptor-Primer Strategy CAPswitch technology can be also effectively be combined with standard, conventional (non PCR-based) technologies well known in the art. As a result, conventional procedures can be significantly simplified, and a full-length cDNA rather than a cDNA fragment library will be generated. In this example, as a starting material for cDNA synthesis, we used poly(A)+RNA. The flow chart in FIG. 4 illustrates the main step of CAPswitch full-length cDNA library construction technology mainly based on the conventional PRE adaptor-primer procedure described by Coleclough et al., (1985). It will be apparent to those skilled in the art that choice of enzymes possessing similar enzymatic activities, structure of CDS primer (PRE adaptor primer), CAPswitch oligonucleotide and vector, and choice of restriction sites used for cloning, as shown in FIG. 4, can be varied without changing the efficiency of the subject procedure. One modification in the procedure can be to first carry out the second-strand synthesis (step 3) followed by restriction digestion (step 2), and cloning into a vector (step 4). Another modification can include using adaptor ligation procedure described in Example 2 instead of restriction digestion (step 2). Use of the vector primer instead of the PRE adaptor-primrer for the first-strand cDNA synthesis (step 1) can also be employed. In this case, the vector primer can have an oligo d(T) sequence at one end to initiate first-strand synthesis and a CAPswitch oligonucleotide sequence at the other end to provide automatic template switching after completion of full-length first-strand cDNA synthesis. Any such variations in the preferred protocol which use CAPswitch technology are within the scope of the invention.

Step 1. Generation of full-length mRNA: cDNA hybrid. 10 pmol of cDNA synthesis primer (CDS3)
CDS2: 5'-d(TCTAGAATTCTCGAGGCGGCCGC(T)$_{30}$VN)-3' (SEQ ID NO. 16)
3'-d(AGATCTTAAGAGCTCCGCCGGCG)-3' (SEQ ID NO. 17)
(where V=G or A or C; N=G or A or T or C) and 10 pmol of CAPswitch oligonucleotide (CSO3):
CSO3: 5'-d(TGCTGCGAGAAGACGACAGAATTCGG)r(GGG)-3' (SEQ ID NO. 18)
were annealed to 5 µg of human skeletal muscle poly(A)+RNA (CLONTECH), in a volume of 12.5 µl of deionized water, by heating the mixture for 2 minutes at 70° C., followed by cooling on ice for 2 minutes. First-strand cDNA synthesis-template switching was then initiated by mixing the annealed primer-RNA with 1000 units of M-MLV RNase H- reverse transcriptase (SuperScript II reverse transcriptase, Life Technologies) in a final volume of 25 µl, containing 50 mM Tris-HCl (pH 8.3 at 22° C.); 75 mM KCl; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and stopped by addition of 75 µl of 150 µg/ml glycogen, 10 mM EDTA. The mRNA:cDNA hybrid was extracted once with phenol/chloroform/isoamyl alcohol (25:24:1, vol/vol), once with chloroform/isoamyl alcohol (24:1, vol/vol), and then precipitated by addition of a half volume of 4 M ammonium acetate (about 40 µl) and 3.7 volumes of 95% ethanol (about 300 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 50 µl of deionized water.

Step 2. Restriction digestion. mRNA:cDNA hybrid generated at step 1 was digested for nondirectional cloning by EcoRI restriction endonuclease (EcoRI and NotI or EcoRI and XhoI for directional cloning) for 1 hour at 37° C. in 100 ml of reaction mixture, containing 50 mM Tris-HCl (pH 7.5), 100 mM NaCl, 10 mM MgCl$_2$, 1 mM DTT, and 50 units of EcoRI restriction endonuclease (New England BioLabs). The reaction was then stopped by addition of 5 µl of 2 mg/ml glycogen, 0.2 M EDTA. The mRNA:cDNA hybrid with EcoRI ends was extracted once with phenol/chloroform/isoamyl alcohol (25:24:1, vol/vol), once with chioroform/isoamyl alcohol (24:1, vol/vol), and then precipitated by addition of a half volume of 4 M ammonium acetate (about 40 µl) and 3.7 volumes of 95% ethanol (about 300 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 5 µl of deionized water.

Step 3. Ligation into vector. The EcoRI-digested mRNA:cDNA hybrid was then ligated to the λgt11 EcoRI vector arm (CLONTECH) overnight at 16° C. under the following conditions: 5 µl of mRNA:cDNA hybrid solution, 50 mM Tris-HCl (pH 7.8 at 22° C.), 10 mM MgCl$_2$, 1 mM DTT, 1 mM ATP, 5% polyethylene glycol (M.W. 8,000), 2.5

μg of λgt11 EcoRI arms, and 2.5 units of T4 DNA ligase (Life Technologies) in a total volume of 20 μl.

Step 4. Second-strand cDNA synthesis. Second-strand cDNA synthesis was carried out in a total volume of 100 μl, containing 20 μl of the vector-ligated mRNA:cDNA hybrid, 20 mM Tris-HCl (pH 7.5 at 22° C.), 100 mM KCl, 10 mM $(NH_4)_2SO_4$, 5 mM $MgCl_2$, 0.15 mM β-NAD, 50 μg/ml BSA, 300 units/ml *E. coli* DNA polymerase I, 12 units/ml *E. coli* RNase H, and 60 units/ml *E. coli* DNA ligase. The reaction mixture was incubated at 16° C. for 1.5 hours and stopped by addition of 4 μl of 2 mg/ml glycogen, 0.2 M EDTA. The ds cDNA was extracted once with phenol/chloroform/isoamyl alcohol (25:24:1, vol/vol), once with chloroform/isoamyl alcohol (24:1, vol/vol), and then precipitated by addition of a half volume of 4 M ammonium acetate (about 35 μl) and 3.7 volumes of 95% ethanol (about 260 μl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 10 μl of deionized water.

The full-length cDNA library was then packaged using standard protocol described in the laboratory manual by Sambrook et al. (1989). In order to confirm the quality of the library generated by CAPswitch technology, we carried out the same quality control experiments as in Example 2 for the PCR-based technology. The size distribution and high efficiency cloning of full-length cDNAs library were similar for both libraries.

These data show that CAPswitch based technology for cDNA library construction based on PRE adaptor-primer strategy generate high quality cDNA libraries with a very high level of full-length cDNA clones.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

| Seq. ID No. | Designation | Sequence information |
|---|---|---|
| 1 | CzR1 | 5'- d(TGTAGCGTGAAGACGACAGAA)r(N)$_{12}$ - 3' |
| 2 | CzR2 | 5'- d(TGTAGCGTGAAGACGACAGAA(N)$_{11}$)r(N)$_1$ - 3' |
| 3 | CzR3 | 5'- d(TGTAGCGTGAAGACGACAGAA(N)$_{11}$) - 3' |
| 4 | CzR4 | 5'- d(TGTAGCGTGAAGACGACAGAAGGATG(N)$_9$)r(N)$_1$ - 3' |
| 5 | Na21-N4 | 5'- d(TGTAGCGTGAAGACGACAGAA)r(N)$_4$ - 3' |
| 6 | Na21-N8 | 5'- d(TGTAGCGTGAAGACGACAGAA)r(N)$_8$ - 3' |
| 7 | NA21-N12 | 5'- d(TGTAGCGTGAAGACGACAGAA)r(N)$_{16}$ - 3' |
| 8 | CDS1 | 5'-d(TCTAGAATTCAGCGGCCGC(T)$_{30}$VN) - 3' (where V = G or A or C; N = G or A or T or C) |
| 9 | CSO1 | 5'-d(CTAATACGACTCACTATAGGGC)r(GGGp)-3' (where p is 3'-phosphate group) |
| 10 | ACT1 | 5' -ACTCGTCATACTCCTGCTTGCTGATCCACATCTGC - 3' |
| 11 | TFR1 | 5' - GTCAATGTCCCAAACGTCACCAGAGA - 3' |
| 12 | CSP1 | 5'- d(CTAATACGACTCACTATAGGGC)- 3' |
| 13 | CSO2 | 5'-d(CTAATACGACTCACTATAGGGC)r(GGG)-3' |
| 14 | Ad1 | 5'- d(AATTCGCGGCCGCGTCGAC) - 3' |
| 15 | Complementary strand to Ad1 | 3' - d(GCGCCGGCGCAGCTGp) - 5' (where p - 3'-phosphate group) |
| 16 | CDS2 | 5'- d(TCTAGAATTCTCGAGGCGGCCGC(T)$_{30}$VN) - 3' (where V = G or A or C; N = G or A or T or C) |
| 17 | Complementary strand to CDS2 | 3'- d(AGATCTTAAGAGCTCCGCCGGCG) - 5' |
| 18 | CSO3 | 5'-d(TGCTGCGAGAAGACGACAGAATTCGG)r(GGG)-3' |
| | | Additional CAPswitch oligonucleotides: |
| 19 | Na21-G | 5'- d(TGTAGCGTGAAGACGACAGAA)r(G) - 3' |
| 20 | Na21-G3 | 5'- d(TGTAGCGTGAAGACGACAGAA)r(GGG) - 3' |
| 21 | Na21-N4G3 | 5'- d(TGTAGCGTGAAGACGACAGAA)r(N$_4$G$_3$) - 3' |
| 22 | Na21-GCGGCN4G3 | 5'- d(TGTAGCGTGAAGACGACAGAA)r(GCGGCN$_4$G$_3$) - 3' |
| 23 | Na21-GTAAG3 | 5'- d(TGTAGCGTGAAGACGACAGAA)r(GTAAG$_3$) - 3' |
| 24 | Na21-GATTG3 | 5'- d(TGTAGCGTGAAGACGACAGAA)r(GATTG$_3$) - 3' |
| 25 | Na21-TGTTG3 | 5'- d(TGTAGCGTGAAGACGACAGAA)r(TGTTG$_3$) - 3' |
| 26 | Na21-CTAAG3 | 5'- d(TGTAGCGTGAAGACGACAGAA)r(CTAAG$_3$) - 3' |
| 27 | Na21-GGTAG3 | 5'- d(TGTAGCGTGAAGACGACAGAA)r(GGTAG$_3$) - 3' |
| 28 | Na21-G2p | 5'- d(TGTAGCGTGAAGACGACAGAA)r(GGp) - 3' |
| 29 | Na21-G3p | 5'- d(TGTAGCGTGAAGACGACAGAA)r(GGGp) - 3' |
| 30 | Na21-G5p | 5'- d(TGTAGCGTGAAGACGACAGAA)r(GGGGGp) - 3' |
| 31 | Na21N-G3 | 5'- d(TGATGCGAGTAGACGACAGAA)r(GGG) - 3' |
| 32 | Na21N-G3p | 5'- d(TGATGCGAGTAGACGACAGAA)r(GGGp) - 3' |
| 33 | Na21ND-G3p | 5'- d(TGATGCGAGTAGACGACAGA)r(GGGp) - 3' |
| 34 | Na21B-G3p | 5'- d(TACGATGCGAGTAGACGACAGAA)r(GGGp) - 3' |
| 35 | Na22-G3 | 5'- d(TGCTGCGAGAAGACGACAGAA)r(GGG) - 3' |
| 36 | Na22-G3p | 5'- d(TGCTGCGAGAAGACGACAGAA)r(GGGp) - 3' |
| 37 | Na22M-G3 | 5'- d(TTGCTGGCAGAAGACGACAGA)r(GGG) - 3' |
| 38 | T7-G | 5'- d(CTAATACGACTCACTATAGGGC)r(G) - 3' |
| 39 | T7-G2 | 5'- d(CTAATACGACTCACTATAGGGC)r(GG) - 3' |
| 40 | T7-G3 | 5'- d(CTAATACGACTCACTATAGGGC)r(GGG) - 3' |
| 41 | T7-G5 | 5'- d(CTAATACGACTCACTATAGGGC)r(GGGGG) - 3' |
| 42 | T7-Gp | 5'- d(CTAATACGACTCACTATAGGGC)r(GP) - 3' |

TABLE 1-continued

| Seq. ID No. | Designation | Sequence information |
|---|---|---|
| 43 | T7-G2p | 5'- d(CTAATACGACTCACTATAGGGC)r(GGp) - 3' |
| 44 | T7-G3p | 5'- d(CTAATACGACTCACTATAGGGC)r(GGGP) - 3' |
| 45 | T7-G5p | 5'- d(CTAATACGACTCACTATAGGGC)r(GGGGGp) - 3' |
| 46 | T7-GCG | 5'- d(CTAATACGACTCACTATAGGGC)r(GCG) - 3' |
| 47 | T7-GCG2 | 5'- d(CTAATACGACTCACTATAGGGC)r(GCGG) - 3' |
| 48 | T7-CG | 5'- d(CTAATACGACTCACTATAGGGC)r(CG) - 3' |
| 49 | T7-DG | 5'- d(CTAATACGACTCACTATA)r(GGGCG) - 3' |
| 50 | T7-N9G3 | 5'- d(CTAATACGACTCACTATAGGGC)r(N$_9$GGG) - 3' |
| 51 | T7-GCG3 | 5'- d(CTAATACGACTCACTATAGGGC)r(GCGGG) - 3' |
| 52 | T7-SUP1 | 5'- d(CTAATACGACTCACTATAGGGCGCGGCCGCCCGGG)r(GCG3) -3' |
| 53 | T7-SUP2 | 5'- d(CTAATACGACTCACTATAGGGCACGCGTGGTCGACGGCCCGG)r(GCG3)-3' |
| 54 | T7-G3-NH2 | 5'- d(CTAATACGACTCACTATAGGGC)r(GGG-NH$_2$) - 3' |
| 55 | T7-G3-BIO | 5'- d(CTAATACGACTCACTATAGGGC)r(GGG-BIO) - 3' |
| 56 | T7-G3-GLY | 5'- d(CTAATACGACTCACTATAGGGC)r(GGG-GLY) - 3' |
| | | (where NH2, BIO and GLY are respectively amino, biotin and glycerol group at the 3'position of ribose residue) |
| 57 | T7-GAG3p | 5'- d(CTAATACGACTCACTATAGGGC)r(GAGGGp) - 3' |
| 58 | T7-GTG3p | 5'- d(CTAATACGACTCACTATAGGGC)r(GTGGGp) - 3' |
| 59 | T7-GGAG2p | 5'- d(CTAATACGACTCACTATAGGGC)r(GGAGGp) - 3' |
| 60 | T7-GGTG2p | 5'- d(CTAATACGACTCACTATAGGGC)r(GGTGGp) - 3' |
| 61 | T7-GACG2p | 5'- d(CTAATACGACTCACTATAGGGC)r(GACGGp) - 3' |
| 62 | T7-GATG2p | 5'- d(CTAATACGACTCACTATAGGGC)r(GATGGp) - 3' |
| 63 | T7-GTTG2p | 5'- d(CTAATACGACTCACTATAGGGC)r(GTTGGp) - 3' |
| 64 | T7-GAGTGp1 | 5'- d(CTAATACGACTCACTATAGGGC)r(GAGTGp) - 3' |
| 65 | T7M-GGAG3p | 5'- d(TCCTAATACGACTCACTATA)r(GGAGGGp) - 3' |
| 66 | T7-GAG3p | 5'- d(CTAATACGACTCACTATAGGGC)r(GAGGGp) - 3' |

References

Kimmel, A. R., S. L. Berger (1987) "Preparation of cDNA and the generation of cDNA libraries: Overview," *Meth. Enzymol.* 152:307–316.

Sonenberg, N., E. Edery, M. Altmann, U.S. Pat. No. 5,219,989, issued Jun. 15, 1993.

Wu, R. ed. (1987) *Methods in Enzymology*, vol. 152, Academic Press, pp. 307–389.

Gubler, U., B. J. Hoffmanm (1983) *Gene* 25:253–269.

Okayama and Berg (1982) *Mol. Cell. Biol.* 2:161–170.

Pruitt, S. C., International Patent. Appl. No. 89110816.9.

Edery, A., L. L. Chu, N. Sonenberg, J. Pelletier (1995) *Mol. Cell Biol.* 15:3363–3371.

Maruyama, K, S. Sugano (1994) *Gene* 138:171–174.

Fromomt-Racine, M., E. B. Pictet, T. Grande (1993) *Nucl. Acids Res.* 21:1683–1684.

Kato, S., S. Sekine, International Patent Publ. No. 0 625 572 A1, Appl. No. 93921061.3 of 22.09.93; Intern. Appl. No. PCT/JP93/01359.

Kato, S. (1994) *Gene* 150:243–250.

Telesnitsky, A, S. Goff (1993) *Reverse Transcnptase* (Skalka, A. M. and Goff, S. P., eds), Cold Spring Harbor Laboratory Press, Cold Spring Harbor, N.Y., pp. 49–83.

Kenan, D. J., D. E. Tsai, J. D. Keene (1994) *Trends Biochem. Sci.* 19:57–64.

Coleclough and Erlitz (1985) *Gene* 34:305–314.

Li, W.-B., C. Gruber, J. Jessee, J.-J. Lin, International Patent. Appl. No. PCT/US94/09038, Publ. No. WO 95/04745; filing date: Aug. 9, 1994; Publ. date: Feb. 16, 1994.

Cheng, S ., International Patent Appi. No.95102141.9; Publ. No. 0 669 401 A2.

Barnes, W. M., U.S. Pat. No. 5,436,149 issued Jul. 25, 1995.

Frohmran, M. A., M. K. Dush, G. R. Martin (1988) *Proc. Natl. Acad. Sci. USA* 85:8998–9002.

Sambrook, J., E. F. Fritsch, T. Maniatis (1989) *Molecular Cloning: A Laboratory Manual*, Cold Spring Harbor Laboratory Press, Cold Spring Harbor, N.Y.

---

We claim:

1. A template switching oligonucleotide capable of selectively interacting with a 5' CAP structure of a full-length mRNA-cDNA intermediate generated by reverse transcription of mRNA, wherein when said template switching oligonucleotide interacts with said 5' CAP structure of said full-length mRNA-cDNA intermediate, said template switching oligonucleotide is capable of serving as a template for additional reverse transcription such that a sequence complementary to said template switching oligonucleotide is incorporated at a 3'-end of a cDNA.

2. The template switching oligonucleotide of claim 1, wherein said template switching oligonucleotide has a general formula: 5'-$dN_1$-$dN_2$- . . . $dNm$-$rN1$-$rN_2$ . . . $rNn$-3'; wherein dN represents a deoxyribonucleotide; m represents an interger, rN represents a ribonucleotide at least one of which is GMP; and n represents an interger.

3. The template switching oligonucleotide of claim 2, wherein m represents an interger of 10 to 50.

4. The template-switching oligonucleotide of claim 2, wherein n represents an interger of 3–7.

5. The template switching oligonucleotide of claim 2, wherein said deoxyribonucleotides are selected from the group consisting of dAMP, dGMP, dCMP, cTMP, modified nucleotides and non-natural nucleotides.

6. The template switching oligonucleotide of claim 2, wherein said ribonucleotides are selected from the group consisting of AMP, GMP, CMP, UMP, modified nucleotides, non-natural nucleotides, and terminator nucleotides.

7. The template switching oligonucleotide of claim 2, wherein said ribonucleotides include at least two GMP ribonucleotides.

8. The template switching oligonucleotide of claim 2, wherein said ribonucleotides include at least three GMP ribonucleotides.

9. The template switching oligonucleotide of claim 2, wherein said template switching oligonucleotide is selected from the group consisting of SEQ ID NO. 1, SEQ ID NO. 2, SEQ ID NO. 4 through SEQ ID NO. 7, SEQ ID NO. 9, SEQ ID NO. 13 and SEQ ID NO. 13 through SEQ ID NO. 66.

10. The template switching oligonucleotide of claim 2, wherein said template switching oligonucleotide comprises a guanylic acid residue at its 3' end, wherein a 3'-OH group of a ribose portion of said guanylic acid residue comprises a chemical group selected from the group consisting of amino, biotin, phosphate and glycerol.

11. The template switching oligonucleotide of claim 2, wherein said template switching oligonucleotide has a general formula: 5'-$dN_{18-30}$-$rG_{3-5}$-3'.

12. The template switching oligonucleotide of claim 2, wherein said deoxyribonucleotide portion of said oligonucleotide comprises at least one restriction site.

13. The template switching oligonucleotide of claim 2, wherein said template switching oligonucleotide comprises a protein portion which binds to a 5' CAP of a mRNA molecule.

14. The template switching oligonucleotide of claim 13, wherein said protein portion is selected from the group consisting of eucaryotic initiation factor 4E and anti-CAP structure antibodies.

15. A method for generating cDNA, comprising the steps of:

combining an RNA sample with a cDNA synthesis primer under conditions sufficient to allow annealing of said cDNA synthesis primer to mRNA in said RNA sample to produce a primer-mRNA complex;

incubating said primer-mRNA complex with enzyme, dNTPs and buffer under conditions which permit template-dependent extension of said primer to generate an mRNA-cDNA hybrid; and contacting said mRNA-cDNA hybrid with the template switching oligonucleotide of claim 1 under conditions which permit template-dependent extension of said cDNA of said hybrid, such that a 3' end of said cDNA sequence of said hybrid comprises a sequence complementary to said template switching oligonucleotide.

* * * * *

UNITED STATES PATENT AND TRADEMARK OFFICE
CERTIFICATE OF CORRECTION

PATENT NO.        : 5,962,271
APPLICATION NO. : 08/582562
DATED             : October 5, 1999
INVENTOR(S)       : Alex Chenchik et al.

It is certified that error appears in the above-identified patent and that said Letters Patent is hereby corrected as shown below:

Title Page, Item (73) Assignee:
The assignee "Cloutech Laboratories Inc., Palo Alto, Calif" should be replaced with "Clontech Laboratories Inc., Palo Alto, Calif"

Signed and Sealed this

Twenty-ninth Day of December, 2009

David J. Kappos
*Director of the United States Patent and Trademark Office*

SEQUENCE LISTING (1) GENERAL INFORMATION:

(iii) NUMBER OF SEQUENCES: 66

(2) INFORMATION FOR SEQ ID NO:1:

(i) SEQUENCE CHARACTERISTICS:
      (A) LENGTH: 33 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:1:

TGTAGCGTGA AGACGACAGA ANNNNNNNNN NNN                                           33

(2) INFORMATION FOR SEQ ID NO:2:

(i) SEQUENCE CHARACTERISTICS:
         (A) LENGTH: 33 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:2:

TGTAGCGTGA AGACGACAGA ANNNNNNNNN NNN                                           33

(2) INFORMATION FOR SEQ ID NO:3:

(i) SEQUENCE CHARACTERISTICS:
         (A) LENGTH: 32 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:3:

TGTAGCGTGA AGACGACAGA ANNNNNNNNN NN                                            32

(2) INFORMATION FOR SEQ ID NO:4:

(i) SEQUENCE CHARACTERISTICS:
         (A) LENGTH: 36 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:4:

TGTAGCGTGA AGACGACAGA AGGATGNNNN NNNNNN                                        36

(2) INFORMATION FOR SEQ ID NO:5:

(i) SEQUENCE CHARACTERISTICS:
         (A) LENGTH: 25 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:5:

TGTAGCGTGA AGACGACAGA ANNNN                                                    25

(2) INFORMATION FOR SEQ ID NO:6:

(i) SEQUENCE CHARACTERISTICS:
         (A) LENGTH: 29 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:6:

TGTAGCGTGA AGACGACAGA ANNNNNNNN                                                29

(2) INFORMATION FOR SEQ ID NO:7:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

```
TGTAGCGTGA AGACGACAGA ANNNNNNNNN NNNNNNN                               37
```

(2) INFORMATION FOR SEQ ID NO:8:

(i) SEQUENCE CHARACTERISTICS:
        (A) LENGTH: 51 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

```
TCTAGAATTC AGCGGCCGCT TTTTTTTTTT TTTTTTTTTT TTTTTTTTTV N               51
```

(2) INFORMATION FOR SEQ ID NO:9:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

```
CTAATACGAC TCACTATAGG GCGGG                                            25
```

(2) INFORMATION FOR SEQ ID NO:10:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

```
ACTCGTCATA CTCCTGCTTG CTGATCCACA TCTGC                                 35
```

(2) INFORMATION FOR SEQ ID NO:11:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

```
GTCAATGTCC CAAACGTCAC CAGAGA                                           26
```

(2) INFORMATION FOR SEQ ID NO:12:

(i) SEQUENCE CHARACTERISTICS:
        (A) LENGTH: 22 bases

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

CTAATACGAC TCACTATAGG GC                                            22

(2) INFORMATION FOR SEQ ID NO:13:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

CTAATACGAC TCACTATAGG GCGGG                                         25

(2) INFORMATION FOR SEQ ID NO:14:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

AATTCGCGGC CGCGTCGAC                                                19

(2) INFORMATION FOR SEQ ID NO:15:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

GTCGACGCGG CCGCG                                                    15

(2) INFORMATION FOR SEQ ID NO:16:

(i) SEQUENCE CHARACTERISTICS:
        (A) LENGTH: 55 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

TCTAGAATTC TCGAGGCGGC CGCTTTTTTT TTTTTTTTTT TTTTTTTTTT TTTVN        55

(2) INFORMATION FOR SEQ ID NO:17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:17:

AGATCTTAAG AGCTCCGCCG GCG    23

(2) INFORMATION FOR SEQ ID NO:18:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:18:

TGCTGCGAGA AGACGACAGA ATTCGGGGG    29

(2) INFORMATION FOR SEQ ID NO:19:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:19:

TGTAGCGTGA AGACGACAGA AG    22

(2) INFORMATION FOR SEQ ID NO:20:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

TGTAGCGTGA AGACGACAGA AGGG    24

(2) INFORMATION FOR SEQ ID NO:21:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

TGTAGCGTGA AGACGACAGA ANNNNGGG    28

(2) INFORMATION FOR SEQ ID NO:22:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

TGTAGCGTGA AGACGACAGA AGCGGCNNNN GGG    33

(2) INFORMATION FOR SEQ ID NO:23:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

TGTAGCGTGA AGACGACAGA AGTAAGGG                                28

(2) INFORMATION FOR SEQ ID NO:24:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

TGTAGCGTGA AGACGACAGA AGATTGGG                                28

(2) INFORMATION FOR SEQ ID NO:25:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

TGTAGCGTGA AGACGACAGA ATGTTGGG                                28

(2) INFORMATION FOR SEQ ID NO:26:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

TGTAGCGTGA AGACGACAGA ACTAAGGG                                28

(2) INFORMATION FOR SEQ ID NO:27:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

TGTAGCGTGA AGACGACAGA AGGTAGGG                                28

(2) INFORMATION FOR SEQ ID NO:28:

(i) SEQUENCE CHARACTERISTICS:
        (A) LENGTH: 23 bases (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:28:

TGTAGCGTGA AGACGACAGA AGG                                               23

(2) INFORMATION FOR SEQ ID NO:29:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:29:

TGTAGCGTGA AGACGACAGA AGGG                                              24

(2) INFORMATION FOR SEQ ID NO:30:

(i) SEQUENCE CHARACTERISTICS:
            (A) LENGTH: 26 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:30:

TGTAGCGTGA AGACGACAGA AGGGGG                                            26

(2) INFORMATION FOR SEQ ID NO:31:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:31:

TGATGCGAGT AGACGACAGA AGGG                                              24

(2) INFORMATION FOR SEQ ID NO:32:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:32:

TGATGCGAGT AGACGACAGA AGGG                                              24

(2) INFORMATION FOR SEQ ID NO:33:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:33:

TGATGCGAGT AGACGACAGA GGG                                    23

(2) INFORMATION FOR SEQ ID NO:34:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:34:

TACGATGCGA GTAGACGACA GAAGGG                                 26

(2) INFORMATION FOR SEQ ID NO:35:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:35:

TGCTGCGAGA AGACGACAGA AGGG                                   24

(2) INFORMATION FOR SEQ ID NO:36:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:36:

TGCTGCGAGA AGACGACAGA AGGG                                   24

(2) INFORMATION FOR SEQ ID NO:37:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:37:

TTGCTGGCAG AAGACGACAG AGGG                                   24

(2) INFORMATION FOR SEQ ID NO:38:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:38:

CTAATACGAC TCACTATAGG GCG                                    23

(2) INFORMATION FOR SEQ ID NO:39:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:39:

CTAATACGAC TCACTATAGG GCGG                                   24

(2) INFORMATION FOR SEQ ID NO:40:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:40:

CTAATACGAC TCACTATAGG GCGGG                                  25

(2) INFORMATION FOR SEQ ID NO:41:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:41:

CTAATACGAC TCACTATAGG GCGGGGG                               27

(2) INFORMATION FOR SEQ ID NO:42:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:42:

CTAATACGAC TCACTATAGG GCG                                     23

(2) INFORMATION FOR SEQ ID NO:43:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:43:

CTAATACGAC TCACTATAGG GCGG                                   24

(2) INFORMATION FOR SEQ ID NO:44:

(i) SEQUENCE CHARACTERISTICS:
        (A) LENGTH: 25 bases (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:44:

CTAATACGAC TCACTATAGG GCGGG                                          25

(2) INFORMATION FOR SEQ ID NO:45:

(i) SEQUENCE CHARACTERISTICS:
            (A) LENGTH: 27 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:45:

CTAATACGAC TCACTATAGG GCGGGGG                                        27

(2) INFORMATION FOR SEQ ID NO:46:

(i) SEQUENCE CHARACTERISTICS:
            (A) LENGTH: 25 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:46:

CTAATACGAC TCACTATAGG GCGCG                                          25

(2) INFORMATION FOR SEQ ID NO:47:

(i) SEQUENCE CHARACTERISTICS:
            (A) LENGTH: 26 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:47:

CTAATACGAC TCACTATAGG GCGCGG                                         26

(2) INFORMATION FOR SEQ ID NO:48:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:48:

CTAATACGAC TCACTATAGG GCCG                                           24

(2) INFORMATION FOR SEQ ID NO:49:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:49:

CTAATACGAC TCACTATAGG GCG                                                   23

(2) INFORMATION FOR SEQ ID NO:50:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:50:

CTAATACGAC TCACTATAGG GCNNNNNNNN NGGG                                       34

(2) INFORMATION FOR SEQ ID NO:51:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:51:

CTAATACGAC TCACTATAGG GCGCGGG                                               27

(2) INFORMATION FOR SEQ ID NO:52:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:52:

CTAATACGAC TCACTATAGG GCGCGGCCGC CCGGGGCGGG                                 40

(2) INFORMATION FOR SEQ ID NO:53:

(i) SEQUENCE CHARACTERISTICS:
        (A) LENGTH: 47 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:53:

CTAATACGAC TCACTATAGG GCACGCGTGG TCGACGGCCC GGGCGGG                         47

(2) INFORMATION FOR SEQ ID NO:54:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:54:

CTAATACGAC TCACTATAGG GCGGG                                                 25

(2) INFORMATION FOR SEQ ID NO:55:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:55:

CTAATACGAC TCACTATAGG GCGGG                                          25

(2) INFORMATION FOR SEQ ID NO:56:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:56:

CTAATACGAC TCACTATAGG GCGGG                                          25

(2) INFORMATION FOR SEQ ID NO:57:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:57:

CTAATACGAC TCACTATAGG GCGAGGG                                        27

(2) INFORMATION FOR SEQ ID NO:58:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:58:

CTAATACGAC TCACTATAGG GCGTGGG                                        27

(2) INFORMATION FOR SEQ ID NO:59:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:59:

CTAATACGAC TCACTATAGG GCGGAGG                                        27

(2) INFORMATION FOR SEQ ID NO:60:

(i) SEQUENCE CHARACTERISTICS:
        (A) LENGTH: 27 bases

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:60:

CTAATACGAC TCACTATAGG GCGGTGG                                              27

(2) INFORMATION FOR SEQ ID NO:61:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:61:

CTAATACGAC TCACTATAGG GCGACGG                                              27

(2) INFORMATION FOR SEQ ID NO:62:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:62:

CTAATACGAC TCACTATAGG GCGATGG                                              27

(2) INFORMATION FOR SEQ ID NO:63:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:63:

CTAATACGAC TCACTATAGG GCGTTGG                                              27

(2) INFORMATION FOR SEQ ID NO:64:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:64:

CTAATACGAC TCACTATAGG GCGAGTG                                              27

(2) INFORMATION FOR SEQ ID NO:65:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:65:

TCCTAATACG ACTCACTATA GGAGGG    26

(2) INFORMATION FOR SEQ ID NO:66:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:66:

CTAATACGAC TCACTATAGG GCGAGGG    27